United States Patent
Armbruster et al.

(10) Patent No.: US 10,947,301 B2
(45) Date of Patent: Mar. 16, 2021

(54) METHOD OF TREATING EXTRACELLULAR TISSUE AND VASCULAR CALCIFICATION AND ARTERIOSCLEROSIS

(71) Applicant: Immundiagnostik AG, Bensheim (DE)

(72) Inventors: Franz Paul Armbruster, Bensheim (DE); Berthold Hocher, Berlin (DE)

(73) Assignee: Immundiagnostik AG, Bensheim (DE)

( * ) Notice: Subject to any disclaimer, the term of this patent is extended or adjusted under 35 U.S.C. 154(b) by 49 days.

(21) Appl. No.: 16/283,012

(22) Filed: Feb. 22, 2019

(65) Prior Publication Data

US 2019/0177403 A1    Jun. 13, 2019

Related U.S. Application Data

(60) Division of application No. 15/436,139, filed on Feb. 17, 2017, now Pat. No. 10,253,092, which is a continuation of application No. PCT/EP2015/069098, filed on Aug. 19, 2015.

(30) Foreign Application Priority Data

Aug. 19, 2014 (DE) ...................... 10 2014 111 859.6

(51) Int. Cl.

| | |
|---|---|
| *A61K 39/00* | (2006.01) |
| *C07K 16/18* | (2006.01) |
| *C07K 16/24* | (2006.01) |
| *A61M 1/34* | (2006.01) |
| *A61K 35/14* | (2015.01) |
| *A61K 35/16* | (2015.01) |
| *G01N 33/68* | (2006.01) |

(52) U.S. Cl.

CPC .............. *C07K 16/18* (2013.01); *A61K 35/14* (2013.01); *A61K 35/16* (2013.01); *A61M 1/3486* (2014.02); *A61M 1/3496* (2013.01); *C07K 16/24* (2013.01); *G01N 33/6893* (2013.01); *A61K 2039/505* (2013.01); *C07K 2317/21* (2013.01); *C07K 2317/24* (2013.01); *C07K 2317/565* (2013.01); *C07K 2317/76* (2013.01); *G01N 2333/47* (2013.01); *G01N 2800/323* (2013.01); *G01N 2800/347* (2013.01)

(58) Field of Classification Search

None
See application file for complete search history.

(56) References Cited

U.S. PATENT DOCUMENTS

| 10,253,092 B2 * | 4/2019 | Armbruster ......... A61M 1/3486 |
|---|---|---|
| 2011/0091379 A1 | 4/2011 | Armbruster et al. |

FOREIGN PATENT DOCUMENTS

| WO | WO-93/01288 A1 | 1/1993 |
|---|---|---|
| WO | WO-00/36919 A1 | 6/2000 |
| WO | WO-2011/000086 A1 | 1/2011 |
| WO | WO-2011/130528 A1 | 10/2011 |

OTHER PUBLICATIONS

C. Dong et al., "Bone Sialoprotein and the Paradox of Angiogenesis Versus Atherosclerosis", irculation Research, vol. 86, No. 8, Apr. 28, 2000, pp. 827-828.
J. J. Kaden et al., "Expression of Bone Sialoprotein and Bone Morphogenetic Protein-2 in Calcific Aortic Stenosis", The Journal of Heart Valve Disease, Jul. 1, 2004, pp. 560-566.
H. Zebger-Gong et al., "1,25-Dihydroxyvitamin $D_3$-induced Aortic Calcifications in Experimental Uremia: Up-Regulation of Osteoblast Markers. Calcium-Transporting Proteins and Osterix", Journal of Hypertension, vol. 29, No. 2, Feb. 1, 2011, pp. 339-348.
D. Ward, "Conventional Apheresis Therapies: A Review", Journal of Clinical Apheresis, vol. 26, No. 5, Jan. 1, 2011, pp. 230-238.
L. W. Fischer et al., "Antisera and cDNA Probes to Human and Certain Animal Model Bone Matrix Noncollagenous Proteins", ACTA Orthopaedica Scandinavica, vol. 66, No. Suppl. 266, Jan. 1, 1995, pp. 61-65.
D. Weismann et al., "Complement Factor H Binds Malondialdehyde Epitopes and Protects from Oxidative Stress", Nature, vol. 478, No. 7367, Jan. 1, 2011, pp. 76-81.
N.S. Fedarko et al., "Factor H Binding to Bone Sialoprotein and Osteopontin Enables Tumor Cell Evasion of Complement-mediated Attack", Journal of Biological Chemistry, American Society for Biochemistry and Molecular Biology, vol. 275, No. 22, Jun. 2, 2000, pp. 16666-16672.
Shanahan et al., 2000, Z. Kardiol. 89 Suppl. 2:63-68 (abstract only).

* cited by examiner

*Primary Examiner* — Elizabeth C. Kemmerer
(74) *Attorney, Agent, or Firm* — Blank Rome LLP

(57) ABSTRACT

A novel therapy concept based on a removal of circulating BSP (bone sialoprotein) from the plasma of patients with chronic kidney disease (CKD) or highly at risk of developing arterial and vascular calcifications. The method comprises method of treatment of extracellular tissue and vascular calcifications, atherosclerosis, arteriosclerosis, and arterial calcification. The beneficial effects of this therapy have been proven by the observed correspondence between levels of circulating free BSP levels and mortality of CKD patients as well as in animal models.

6 Claims, 8 Drawing Sheets

Specification includes a Sequence Listing.

METHOD OF TREATING EXTRACELLULAR TISSUE AND VASCULAR CALCIFICATION AND ARTERIOSCLEROSIS

CROSS REFERENCE TO RELATED APPLICATIONS

This is a divisional of U.S. application Ser. No. 15/436,139, filed on Feb. 17, 2017, now U.S. Pat. No. 10,253,092, which is a continuation of International Application No. PCT/EP2015/069098, filed on Aug. 19, 2015, which claims priority to German patent application No. 10 2014 111 859.6, filed on Aug. 19, 2014, each of the prior applications is incorporated herein in its entirety.

FIELD OF THE INVENTION

The present invention relates to a method for treating long-term symptoms and side-effects of chronic kidney disease, notably extracellular tissue and vascular calcification, atherosclerosis (arteriosclerosis) and arterial and vascular calcification.

BACKGROUND OF THE INVENTION

Chronic kidney disease (CKD), also known as chronic renal disease (CRD) affects about 10% of the population in Europe and North America. CKD is characterized by a progressive loss in renal function over a period of months or years. The Kidney Disease Improving Global Outcomes (KDIGO) statement has defined CKD as either kidney damage or reduced glomerular filtration rate (GFR) to less than 60 mL/min/1.73 m2 sustained for more than 3 months (cf. KDIGO Clinical Practice Guideline for the Diagnosis, Evaluation, Prevention, and Treatment of Chronic Kidney Disease-Mineral and Bone Disorder (CKD-MBD, Kidney Int 76; Suppl. 113, 2009). There is no specific treatment unequivocally shown to slow the worsening of CDK except for cases where there is a specific underlying cause to CKD such as vasculitis. A permanent kidney failure then requires a renal replacement therapy which may be a form of dialysis or a kidney transplant. As CKD progresses and GFR declines, mineral metabolism disturbances increase and hyperphosphatemia occurs along with a reduction in renal 1a-hydroxylation of 25-hydroxyvitamin D and low circulating levels of calcitriol which in turn cause a decrease of intestinal calcium absorption. The disturbed calcium and phosphate homeostasis causes variable degrees of hypocalcaemia and secondary hyperparathyroidism, with concomitant abnormalities in bone turnover and metabolic bone disease. The mineral and bone disorder (MBD) is a common manifestation of CKD. Other symptoms of CKD include increase blood pressure, iron deficiency anaemia, metabolic acidosis, azotemia and uraemia, an activation of the sympathetic tone, inflammation and oxidative stress. CDK goes therefore in line with high morbidity and mortality. CKD patients suffer in particular from accelerated atherosclerosis and tissue calcification. CKD patients on dialysis or with end stage renal disease (ESRD) are more likely to die from cardiovascular complications than from kidney failure (M. Kettler et al., Nephrology 2009, 14: 389-394).

The progress of arterial and vascular calcification is linked to a dysregulated mineral metabolism and altered levels of serum calcium and calcium-phosphorus products. The elevated extracellular levels of these minerals further affect the survival and phenotype of vascular smooth muscle cells and myocardial cells. The calcification, mostly as calcium hydroxyl apatite deposits, may occur in blood vessels, the myocardium and cardiac valves. In the arterial vessel wall, calcification takes place in the intima or in the media. Medial calcification (also referred to as Monckeberg sclerosis) is the form classically associated with age, diabetes and CKD.

Conventional therapeutic approaches are usually directed to bringing the biochemical parameters to ranges associated with lower mortality. They comprise (a) a use of an adapted dialysate calcium concentration; (b) a use of phosphate-binding agents; (c) the administration of calcitriol or vitamin D analogues; (d) the use of calcimimetics; (d) diet recommendations (reducing dietary phosphate intake and administering phosphate binders and calcium supplements); and/or (e) the uptake of native vitamin D supplements. WO 2011/000086 A1 (University of Alberta) discloses a method and apparatus for reducing serum phosphate levels and calcium product in patients by hemodialysis since observational data suggest that higher doses of calcium-based phosphate binders may contribute to vascular calcification. There is generally a considerable interest in controlling serum phosphate while minimizing oral calcium load. On the other hand, most phosphate is intracellular and thus unavailable to hemodialysis. WO 2011/130528 A (Fresenius Medical Care Holdings Inc.) discloses an extracorporeal blood treatment system including a calcium trap wherein an immobilized species is adapted to reduce the calcium concentration in the blood to a concentration that prevents blood clotting thereby producing calcium-depleted blood. However, there are no specific drugs or intervention methods available for interfering with the pathogenesis of vascular and tissue calcification. There is also a need for more drugs and intervention methods against the cardiovascular risks concomitant CKD, ESRD and renal replacement therapies. The prior art therefore represents a problem.

SUMMARY OF THE INVENTION

The object of the invention is achieved by a method and medicament for treating extracellular tissue and vascular calcification, atherosclerosis, arteriosclerosis, and arterial calcification and the cardiovascular risks concomitant CKD, ESRD and renal replacement therapies comprising use and administration of an effective amount of a receptor molecule recognizing human bone-sialoprotein (BSP) in blood, plasma or serum. The medicament may be a human monoclonal antibody or a humanized monoclonal antibody or a rat monoclonal antibody. The medicament may preferably be an antibody which comprises one or more functional portions of a protein sequence as disclosed in any of SEQ ID NOS: 1, 2, 3, 4, 5, and 6. Functional or essential portion means in this connection portion of the molecular which take part in the detection and binding of human BSP in plasma. Not comprised are therefore linker portions, leader sequences which are cut off during protein maturation, or interchangeable portions of the antibody. An essential portion of the receptor molecule or antibody therefore relates to the one or more of complement determining regions (CDR) contained in any of the sequences with SED ID NO: 1, 2, 3, 4, 5, and 6, as those are required for recognition and binding of human BSP in plasma or serum. Conservative protein substitutions and insertions are known to those skilled in the art.

The invention further comprises a method wherein the receptor molecule recognizes an antigen determinant or epitope of BSP which is accessible in plasma and bound by an antibody having any protein sequence of SEQ ID NO: 1, 2, 3, 4, 5, and 6. The term tissue and vascular calcification shall encompass the cardiovascular risks concomitant CKD, ESRD and renal replacement therapy and also comprise the terms arteriosclerosis and atherosclerosis. While CKD is generally associated with increased risk of coronary heart disease the knowledge with respect to the histopathologic characteristics of coronary atherosclerosis in individuals with CKD is scarce and the terms arteriosclerosis and atherosclerosis, while intrinsically relating to different etiologies, often used interchangeably. However, the frequencies of advanced atherosclerotic lesion due to arterial calcifications is increasing with a concomitant decrease of the GTR. On the other hand, there is also a strong link between total cholesterol, calcium-phosphorus product, diabetes, hypertension, serum creatinine and cardio-vascular risks.

The disclosure further relates to a receptor molecule or antibody which may be comprised in a diagnostic system or kit, preferably a kit for companion diagnostic of renal replacement therapy, dialysis, CKD, ESRD, tissue and vascular calcification, atherosclerosis, arteriosclerosis, arterial calcification. The companion diagnostic may in particular also relate to an evaluation of the risks for arteriosclerotic lesions in individuals with CKD or ESRD, and for an evaluation of the cardiovascular risks in general.

BRIEF DESCRIPTION OF THE DRAWINGS

The present invention is best understood when read in conjunction with the accompanying figures, which serve to illustrate the preferred embodiments. It is understood, however, that the invention is not limited to the specific embodiments disclosed in the figures.

DETAILED DESCRIPTION OF THE INVENTION

Figure 1:
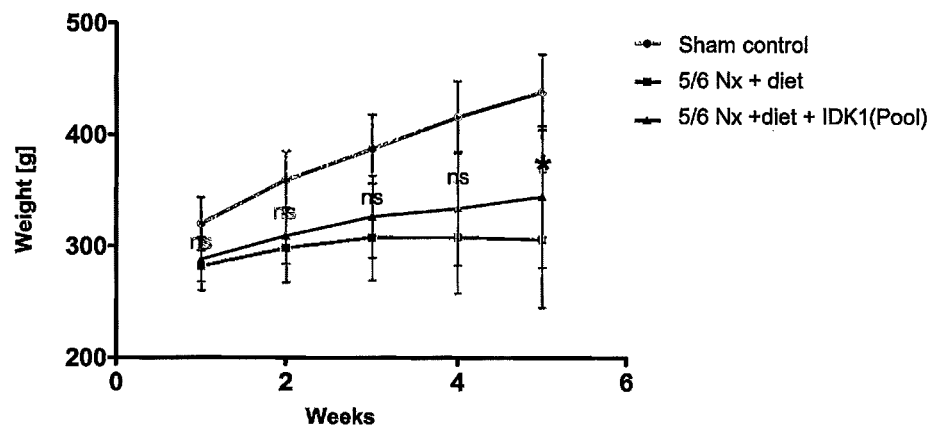
FIG. 1 is a diagram of the body weights of rats subjected to sham surgery (healthy), 5/6 Nx nephrectomy 5 (uremic calcification) and 5/6 Nx as well as anti-BSP-IDK1 mAb therapy during five weeks of uremic calcification diet (high phosphate, calcium and calcitriol) as described in example 2.

The present invention provides a novel therapy concept based on a removal of circulation BSP (bone sialoprotein) from the plasma of patients with chronic kidney disease (CKD), preferably by plasmapheresis or an administration of antibodies against BSP in plasma. The present invention further provides a BSP absorber material for plasmapheresis and a pharmaceutical composition for direct administration which are biocompatible in humans. The beneficial effects of this therapy have been proven by the observed correspondence between levels of circulating free BSP levels and mortality of CKD patients.

The mechanism of arterial calcification is complex, but without wishing to be bound by any theory, the first step appears to be a de-differentiation or transformation of vascular smooth muscle cells (VSMC) into an osteoblast/chondrocytic phenotype. VSMCs originate from a similar mesenchymal stem cell as osteoblasts. It is believed that transcription factor core binding factor a1 (Cbfa-1; encoded by the RUNX2 gene) is responsible for the phenotypic transformation of VSMCs to osteoblast cells. The signals that induce a transformation to an osteoblast/chondrocytic phenotype, however, are multiple. In both bone and arteries, there are inhibitors of calcification, including matrix gla proteins, pyrophosphate, and osteopontin, and circulating inhibitors such as fetuin-A. Calcification occurs if there is an imbalance between inhibitors of calcification and pro-mineralizing factors that stimulate VSMC de-differentiation.

Bone sialoprotein (BSP), a phosphorylated glycoprotein, is an important component of extracellular matrix. BSP is usually expressed by cells which take part in the formation of dentin, bones and cartilage but it also an adhesion molecule which can bring about attachment of cells on the tissue matrix. BSP binds to the integrin receptors through its recognition sequence (arginine-glycine-aspartate, RGD). BSP forms in vitro crystallization nuclei for biological apatite and in vivo it takes part in mineralization. The switching off of the BSP gene in knock-out mice leads however to no recognizable disruption of the building and functioning of the skeleton. On the other hand, BSP is involved in tissue calcification as its binding to collagen is needed to initiate bone mineralization and the adhesion of osteoblasts to the mineralized matrix (Ogata Y, J. Periodontal Res. 2008, 43(2): 127-135). WO 00/36919 discloses a suppression of the expression of BSP in tumor and connective tissue cells which promote calcification. In vitro studies suggest that BSP is involved in the transformation from VSMC to osteoblast-like cells and that a pharmacologically reduced expression of BSP may lead to a deceleration of this transformation process. By immune-histochemical methods we also discovered BSP in the core of aortal calcifications from uremic, calcitriol treated rats (D. Haffner et al., J Hypertens 2005, 23(5): 1067-75). Cell culture experiments with VSMC suggest that calcitriol causes an up-regulation of pro-mineralizing genes, including BSP (H. Zebger-Gong et al., J Hypertens. 2011, 29(2): 339-48).

While BSP plays an important role in bone turnover literature suggests that an elimination of circulating BSP poses no risk regarding bone health. BSP knockout mice only show a reduction in bone turnover, with a reduced recruitment of osteoclasts. Mice over-expressing BSP have an elevated bone turnover as evidenced by elevated calcium and reduced PTH levels. There is however no clinical or other evidence that an elimination of BSP from plasma may cause osteoporosis. Postmenopausal woman suffering from osteoporosis show elevated levels of serum BSP compared to perimenopausal healthy controls. Treatment with alendronic Acid® (INN) as well as hormone replacement therapy, both established treatment options of osteoporosis, lead to a reduction of serum BSP levels in postmenopausal women.

Calcified lesions contain osteoblasts, osteoclasts, trabeculae and numerous proteins regulating calcification such as osteopontin, alkaline phosphatase and bone sialoprotein. More precisely, we have discovered an immunostaining for BSP and other pro-mineralizing proteins regulating calcification prior overt calcification in the arteries of ESRD patients. This has lead us to the assumption that a deposition of BSP precedes calcification so that it could be target for specific inhibition of tissue and arterial calcification. As BSP has such a central role in the calcification progress we initiated experiments on whether vascular and soft tissue calcification is reduced and the overall outcome of renally impaired patients with CKD or ESRD is improved by interfering with this protein using therapeutic antibodies. Alternatively, BSP may be removed from circulation using plasmapheresis. Our new therapeutic approach aims at reducing uremic vascular and soft tissue calcification and improving overall outcome of CKD by modulating the concentrations of circulating BSP in plasma. This may be achieved by the development of a plasmapheresis intervention that eliminates excess BSP from the circulation in a hemodialysis process.

Initial experiments conducted in uremic rats subjected to a 5/6 nephrectomy (5/6Nx) indicate that the administration of an anti-BSP-antibody goes in line with decreased calcification, decreased media-to-lumen ratio of intrarenal vessels and decreased perivascular fibrosis of intrarenal vessels. Thus, we have adapted the novel therapy concept to a medical device using plasmapheresis to remove BSP from patients.

EXAMPLES

Example 1—Method of Inducing Vascular and Tissue Calcification in Rats

Among the available experimental models, the 5/6 nephrectomy (5/6 Nx) of rats is most used for studies of progressive renal disease. This is because the features of this experimental procedure are common to CKD observed in humans [S. Kren et al., "The course of the remnant kidney model in mice," Kidney Int. 1999; 56:333-337]. The 5/6 nephrectomy has also been established to test new therapies and has been proven to be clinically relevant [C K Fujihara et al., Losartan-hydrochlorothiazide association promotes lasting blood pressure normalization and completely arrests long-term renal injury in the 5/6 ablation model. Am J Physiol Renal Physiol. 2007; 292:F1810-1818; F. Terzi et al., "Sodium restriction decreases AP-1 activation after nephron reduction in the rat: role in the progression of renal lesions," Exp Nephrol. 2000; 8:104-114; F. Waanders et al., "Effect of renin-angiotensin-aldosterone system inhibition, dietary sodium restriction, and/or diuretics on urinary kidney injury molecule 1 excretion in nondiabetic proteinuric kidney disease: a post hoc analysis of a randomized controlled trial," Am J Kidney Dis. 2009; 53:16-25]. The 5/6 nephrectomy can be performed by unilateral nephrectomy and either partial infarction or amputation of the poles of the remaining kidney [L. S. Santos et al., "Surgical reduction of the renal mass in rats: morphologic and functional analysis on the remnant kidney," Acta Cir Bras. 2006; 21:252-257].

Male Wistar rats weighing about 100 g were used for all experiments. They were subjected to a 5/6 nephrectomy by two surgeries within two weeks. One week after the first surgery, the kidney remnant rats were further fed a diet comprising 1.2% phosphate and 0.9% calcium to induce tissue and vascular calcification. One week after the second surgery the animals further received oral doses of calcitriol of 0.25 mg/kg which suppresses parathyroid hormone production. The calcitriol administration further promotes vascular calcifications by several mechanisms: (i) an increase in intestinal calcium and phosphate absorption; (ii) over-suppression of parathyroid hormone resulting in low bone turnover disease and diminished calcium delivery to the bone; and (iii) direct effects on the vascular wall. Thus, we specifically examined in the instant animal experiment the calcification of arterial vessels of sham and remnant kidney rats (Wistar) subjected to a phosphate and calcium enriched diet and additional doses of active vitamin D. The therapy of the invention was tested by treating the kidney remnant rats by a subcutaneous administration of various doses of a rat IgG monoclonal antibody specific for circulating soluble bone sialoprotein (BSP). No hypersensitivity or adverse side reactions of the mAb therapy against soluble BSP were observed, in particular no allergic reactions or inflammations. The systemic response was good and no side effects observed. No changes in blood pressures were observed between healthy and nephrectomized rats during the text period.

Results were obtained for rats subjected to sham surgery and diet only (n=10), 5/6 Nx rats receiving placebo (n=14), and 5/6 Nx rats receiving a therapy with 5 monoclonal rat antibody specific for circulating soluble bone sialoprotein (anti-BSP-mAb): low dose therapy (n=14; 3 mg mAb/kg/week); medium dose (n=14; 10 mg mAb/kg/week) and high dose (n=14; 30 mg/kg/week). The uremic control was represented by 5/6 Nx rats (n=10) receiving a high phosphate and calcium diet but no calcitriol. Aortic medial calcification can be reduced vis-ci-vis untreated controls by a 10 systemic treatment with the matrix metalloproteinase inhibitor such as doxycycline (X. Qin et al., "*Matrix metalloproteinase inhibition attenuates aortic calcification*," Arterioscler Thromb Vase Biol 2006; 26: 1510-1516). Thus, a further control group consisted of 5/6Nx rats (n=14) receiving a phosphorous calcium diet as well as doses of doxycycline (n=14); control (n=6).

The rat blood pressures were measured non-invasively first time three days after the first treatment with anti-BSP mAb by determining the tail blood volume with a sensor and an occlusion tail cuff. The treatments by anti-BSP mAbs were repeated in weakly intervals using low, medium, and high doses, respectively. Five weeks after the first treatment by anti-BSP mAbs, tail blood was taken and the animals 20 killed by a use of isoflurane gas. The organs (kidney, heart, aorta) were taken for further histological analyses: von Kossa staining for quantifying mineralization and calcification in tissue sections; Sirius Red staining (connective tissue staining) for quantifying interstitial and perivascular fibrosis; Elastica van Gieson staining (connective tissue staining solution) for determining the media to lumen ratio in cardiac 25 and renal vessels; PAS diastase staining for determining glomerulosclerosis; by wet chemistry for the presence of calcium and phosphate products; by Western blotting for collagen I, collagen II, TGF-ß1, SMAD-2, CTGF; and by RT-PCR for TRP5, P21, VDR, MMP2, MMP9, osteopontin, ANP, TRPV6, calbindin, BSP, CBFA1, osterix, osteocalcin. Measured blood plasma parameters: creatinine, calcium, phosphate, magnesium, fetuin A, FGF-23, beta2-microglobulin; calbindin, clusterin, cystatin-C, NGAL, osteopontin, TIMP-1, VEGF.

Example 2—Results of the Anti-BSP mAb Therapy in Rats

Visual Inspection of Aorta and Remnant Kidney

The organs were taken at end and visually inspected. The aortas from healthy (sham) animals showed no signs of aortic calcification, no atherosclerotic intima lesions and no 'artheriosclerotic' intima/media lesions. The aortas from 5/6 Nx kidney remnant rats, which had received a phosphorus calcium diet and calcitriol, showed massive aortic calcifications and dilated aorta brackets. The thoracic and abdominal regions of the aortas of the Nx rats further showed dilated calcified brackets. Whereas healthy (sham) animals showed no symptoms for a kidney disease, the remnant kidneys of the 5/6 Nx rats were edematous enlarged and whitely colored as typical for uremic calcification.

Body Weight

The body weight of healthy (sham) and 5/6 Nx rats were significantly different after five weeks. The body weights of the healthy animals increased gradually during the five weeks period whereas the body weights of placebo-treated 5/6 Nx rats increased at the beginning and decreased with progressing calcification treatment. On the other hand, the body weights of anti-BSP mAb treated 5/6 Nx rats increased during the entire period of five weeks so that the body weights of anti-BSP-mAb treated animals were significantly higher than for untreated animals. These results have been summarized in FIG. 1. Thus, 5/6 Nx rats which had undergone an anti-BSP-mAb therapy had significantly higher body weights compared to controls after 5 weeks (*p<0.05 mAb-BSP therapy pooled compared with 5/6 Nx controls).

Mortality

The mortality of placebo-treated 5/6 Nx rats (4 out of 14 after four weeks) was significantly higher compared to rats which had received a low, medium, or high dose anti-BSP mAb treatment (2/14 and 4/14 and 2/14) or sham (0/10) only.

Cystatin C and Kidney Function

Figure 2:
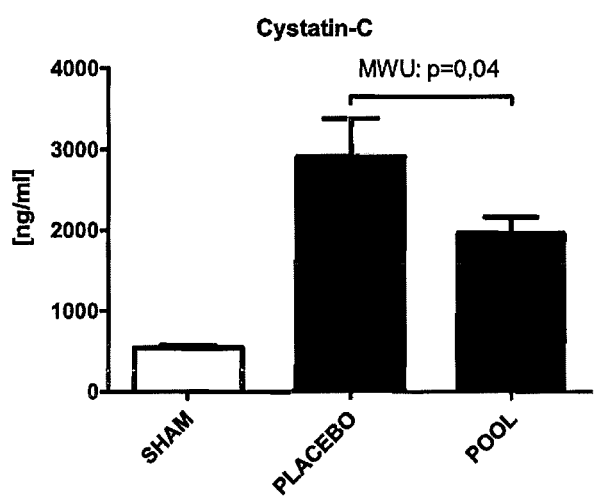
FIG. 2 is a column diagram summarizing the effect of the anti-BSP mAb therapy on basis of the media to lumen ratio (intrarenal arteries) and of renal perivascular fibrosis, again for rats subjected to sham surgery, 5/6 Nx and placebo treatment and 5/6 Nx and anti-BSP IDK1 mAb therapy after five weeks of uremic calcification diet as described.

The plasma level of cystatin C is a parameter reflecting the glomerular filtration rate (GFR) and kidney function. FIG. 2 is a column diagram comparing the plasma cystatin C levels for 5/6 Nx rats which had received an anti-BSP-mAb therapy (pooled for low, medium and high dose therapy) and 5/6 Nx rats which received a treatment with a placebo. The Mann-Whitney U test (MWU) of the data supports significantly lower cystatin C values for 5/6Nx animals (pooled) which had received an anti-BSP mAb therapy compared to untreated 5/6 Nx controls (***p<0.0001).

Histological Examination of Kidneys

Figure 3:
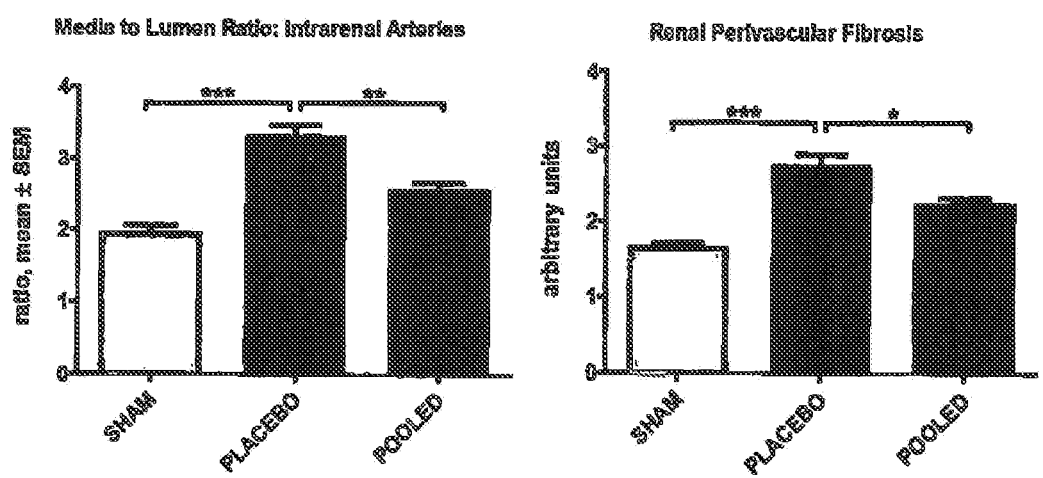
FIG. 3 is a column diagram summarizing the effect of an anti-BSP IDK1 mAb treatment on plasma levels of cystatin-C for healthy and renally impaired rats as described in example 2.
Figure 4:
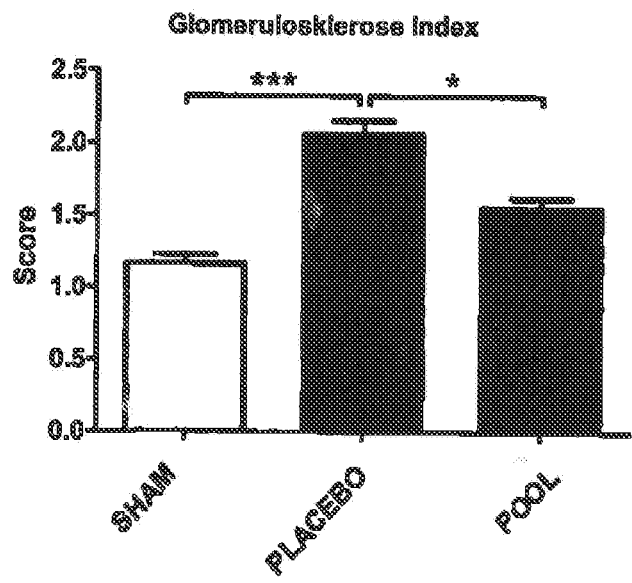
FIG. 4 is a column diagram summarizing the effects of an anti-BSP IDK1 mAb treatment on the glomerulosclerosis index.

The kidney were histologically examined after staining. No large differences could be detected after the von Kossa staining for calcium products. The Sirius Red staining showed a trend to reduced interstitial fibrosis, and the PAS staining a significantly reduced glomerulosclerosis (see FIG. 4) and media to lumen ratio (FIG. 3 A/B) for 5/6 Nx rats which had received an anti-BSP therapy. More precisely, 5/6 Nx rats subjected to an anti-BSP mAb therapy had significantly less glomerulosclerosis compared to untreated 5/6 Nx controls (***p<0.0001; *p<0.05); anti-BSP treated 5/6 Nx rats also showed a significantly reduced media to lumen ratio compared to untreated controls at intrarenal vessels as well as a reduced perivascular fibrosis.

Analysis for Matrix Proteins and Expression of Vitamin D Receptor.

Figure 5:
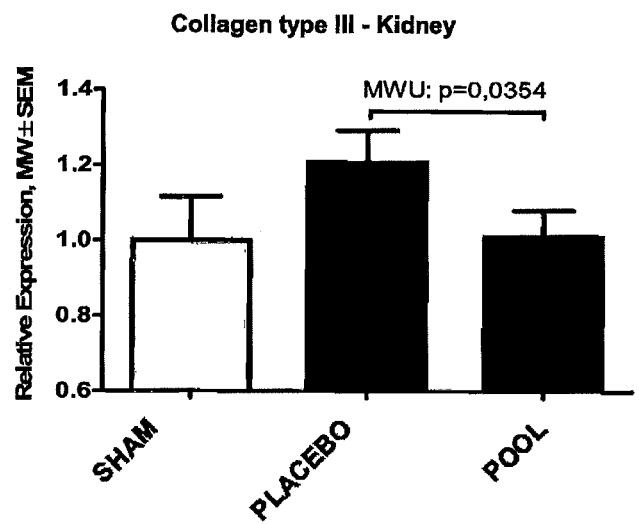
FIG. 5 is a column diagram summarizing the effect of an anti-BSP IDK1 mAb treatment on renal collagen III.

5/6 Nx rat subjected to an anti-BSP mAb therapy showed a trend to a lowered expression of the matrix protein collagen I and collagen III (FIG. 5) when analyzed by Western blot analysis, compared to placebo treated rats and sham. The standard deviation of the results however was high so that the result is only significant for collagen III. The RT-PCR expression analysis for renal vitamin D receptor shows that the anti-BSP mAb therapy seems to bring about an up-regulation of the vitamin D receptor compared to placebo-treated 5/6 Nx rats and sham (see FIG. 4). The wet chemical analysis of the renal calcium phosphorus product produced no significant differences.

Heart and Aorta

Figure 6:
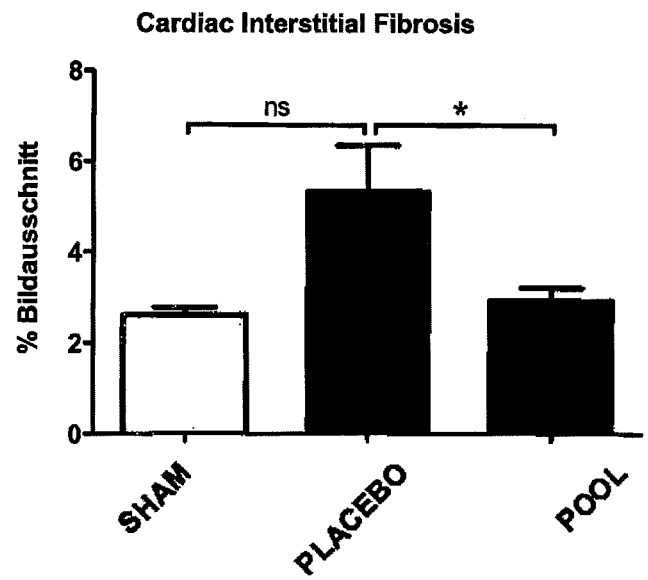
FIG. 6 is a column diagram summarizing the effect of an anti-BSP IDK1 mAb treatment on cardiac interstitial fibrosis.
Figure 7:
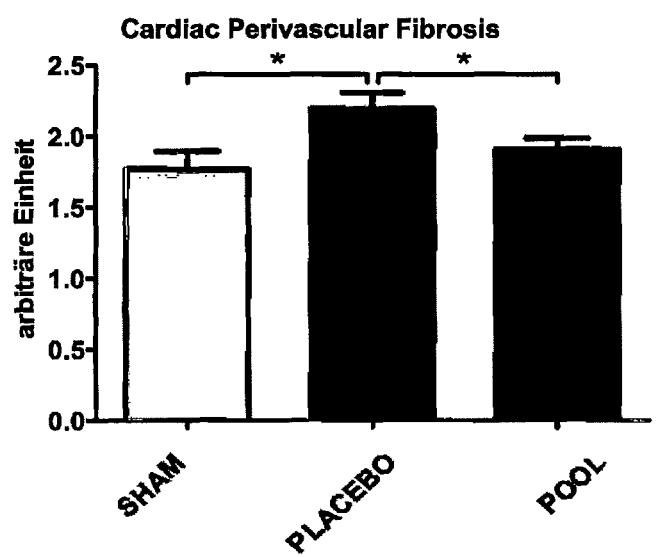
FIG. 7 is a column diagram summarizing the effect of an anti-BSP IDK1 mAb treatment on cardiac perivascular fibrosis.

The histological examination of the heart showed a significantly reduced interstitial fibrosis for 5/6 Nx rats (FIG. 6) receiving an anti-BSP IDK1 mAb therapy. The therapy also reduced cardiac perivascular fibrosis significantly (see FIG. 7). The results were significant compared to placebo-treated controls and sham (*p<0.0001; *p<0.05). The analyses for proteins indicated again that the described therapy may lead to a reduced cardiac expression of the matrix protein collagen III and of TGFß-1, usually associated with fibrotic processes, compared to placebo-treated 5/6 Nx controls and sham.

Figure 8:
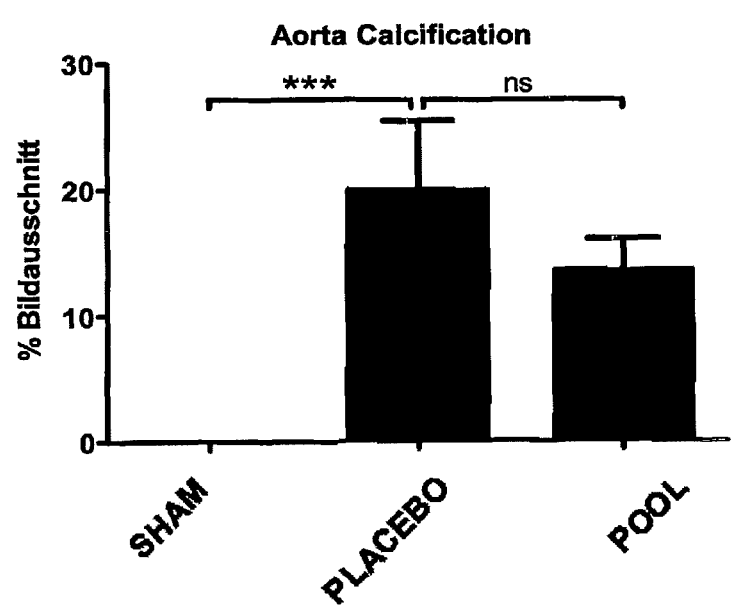
FIG. 8 is a column diagram summarizing the effect of the anti-BSP IDK1 mAb therapy on the calcification of the aorta.
Figure 9:
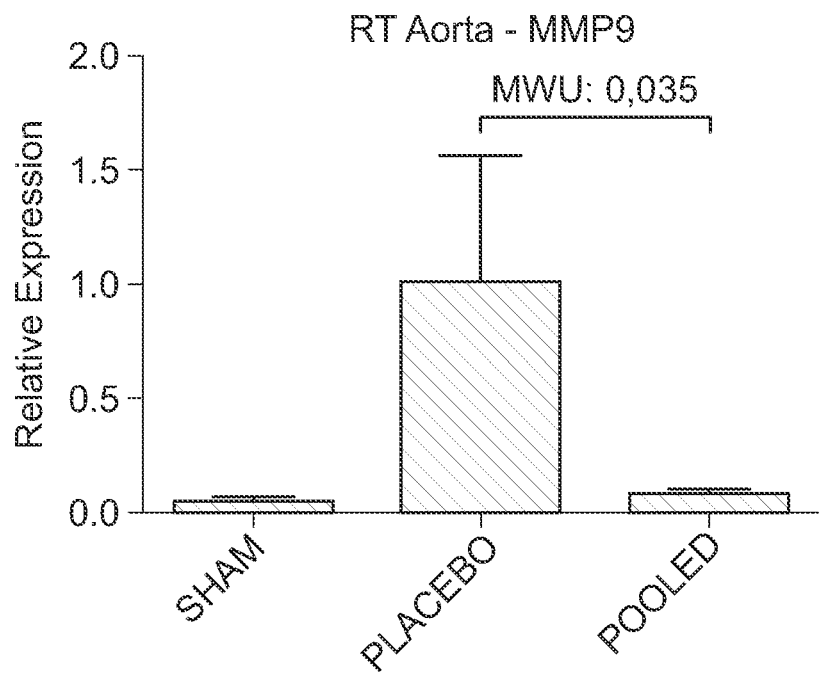
FIG. 9 is a column diagram summarizing the effect of the anti-BSB IDK1 mAb therapy of RT aorta—MMP9.

While the total aortic calcification (FIG. 8) did not differ significantly in the aortas the wet chemical analyses showed a significantly reduced amount of phosphorous deposits. The RT-PCR analyses further support a reduced expression of the metalloprotease MMP9 (FIG. 9) compared to placebo-treated 5/6 Nx rats.

Thus, the results support that an administration of an antibody binding to a non-precipitated or soluble form of bone sialoprotein in plasma has a significant effect on tissue and vascular calcification in the chosen animal model for CKD. In summary: Von Kossa staining of aorta sections showed that extensive aortic calcifications were present in calcitriol-treated uremic rats. In contrast, no calcifications were observed in sham animals and the anti-BSP antibody treatment was able to decrease calcification. Anti-BSP-antibody treated animals also had a significantly decreased media-to-lumen ratio of intrarenal vessels and less perivascular fibrosis of intrarenal vessels. These results are very promising and give reason to believe in the possibility to use the anti-BSP-antibody to prevent vascular and arterial calcification in patients with CKD or ESRD.

The results for BSP elimination by an anti-BSP-antibody in the conducted experiment showed also impressive antifibrotic effects in the kidney and the heart. However, it is not clear, whether the observed antifibrotic effects are due to a reduced calcification, or whether the antibody has antifibrotic activity. Thus, it is contemplated to investigate the antifibrotic properties of the anti-BSP-antibody in an animal model of diabetic kidney disease, with fibrosis being one of the main characteristics of the chosen model. For this, we contemplate using another different rat model of vascular calcification in order to confirm the beneficial effects of anti-BSP-antibody under different circumstances.

Example 3—Antibodies Binding to BSP in Plasma

BSP is bound in plasma by complement factor H with high affinity. There have been produced antibodies against peptide partial structures of BSP (L. W. Fisher et al., Acta Orthop Scand Suppl., 1995, 266, 61-655), against recombinant BSP (J. T. Stubbs 3rd et al., J. Bone Miner. Res. 1997 12(8), 1210-22), and against BSP isolated from bones, which antibodies failed to bind any BSP in plasma or serum. As the larger factor H molecule of 150 kDa seems to mask the smaller BSP of ca. 65 kDa (N. S. Fedarko et al., J. Biol. Chem., 200, 275, 16666-16672; WO 00/062065) we screened for an antibody which cross-reacts with BSP (rat or human) in serum or plasma, or a BSP fragment thereof, and this even in the presence of factor H or endogenous BSP receptors.

For this purpose we used conserved peptide epitopes from the human BSP sequence, more precisely, from human BSP II disclosed at UniProtKB/SWISS-PROT:P21815 (SIAL_HUMAN) and its natural variants at positions 195, 213, 219, 256, 268 and 270. As the human BSP further is a phosphorylated glycoprotein with phosphorylated serine at positions 31, 67, 74, 75. 94. 100, 149, 280; sulphated tyrosine and multiple complex glycosylation, we were looking specifically for potential peptide epitopes. Moreover, we prepared a multiplicity of rat monoclonal antibodies against BSP epitopes common in rat and human, coupled to a carrier, and tested the rat mAbs for binding to human BSP in plasma. For increasing the antigenicity we further used synthetically coupled BSP epitopes as described in EP1888631 B1 as well as BSP epitopes coupled with beta-alanine. Preferred artificial BSP epitopes for immunization and screening of the antibody libraries are indicated below:

SEQ ID NO: 1

YTGLAAIQLPKKAGDZ wherein Z represents one or more beta-alanine.

SEQ ID NO: 2

SENGEPRGDNYRAYEDEYSYFKGQGYDGYDGQNYYHHQZ wherein Z represents one or more beta-alanine.

SEQ ID NO: 3

ZEDA_T_PG_T_QYTGLAAIQLPKKAGZSGGGGSAZGAKKPLQIAALGTYG_T_GP

_T_ADEZ wherein Z represents one or more beta-alanines. The peptide of SEQ ID NO: 3 has been derived from a human BSP wherein multiple accessible BSP epitope have been coupled using a spacer sequence such as SGGGGS.

We screened differentially a synthetic human antibody library for an antibody reacting with synthetic peptide epitopes derived and common to rat or human BSP which we assumed being accessible in plasma. Moreover, we screened a proprietary synthetic human antibody library (mAB-Factory GmbH, Braunschweig, DE), prepared in accordance with DE 4122599 C2 and WO 93/01288 (PCT/EP92/01524), for phagemid-expressed single chain antibodies binding to BSP peptide epitopes with a soluble peptide antigen as indicated and with human BSP in plasma. A respective full human antibody (AF165R4.2-E2) specific for human BSP in plasma was obtained and reconstructed.

Further, we isolated and sequenced a rat monoclonal antibody (anti-BSP_IDK1), and a partial proprietary humanized antibody library comprising humanized variants of the rat complementary determining region which binds to human BSP in plasma with high affinity. Moreover, a chimeric CDR-grafted human monoclonal antibody was obtained.

As there are no hard and fast rules for choosing the human acceptor frameworks into which to graft the donor CDRs, we disclose herein below the sequences of our fully human anti-hBSP antibody which binds to human BSP in plasma as well as of the CDR grafted chimeric antibody and the humanized monoclonal antibody which CDRs are based on the CDR of the rat monoclonal antibody (anti-BSP IDK1):

HEAVY CHAIN (AF 165R42-E2)

SEQ ID NO: 4

MGWSCIILFLVATATGAHSQLVQSGAEVKKPGASVKVSCKASGYTFTGYYMHWVRQAPGQGL

EWMGRINPNSGGTNYAQKFQGRVTMTRDTSISTAYMELSRLRSDDTAVYYCARSQGATGF

DPWGQGTLVTVSSASTKGPSFVPLAPSSKSTSGGTAALGCLVKDYFPEPVTVSWNSGALT

SGVHTFPAVLQSSGLYSLSSVVTVPSSSLGTQTYICNVNHKPSNTKVDKKVEPKSCDKTH

TCPPCPAPELLGGPSVFLFPPKPKDTLMISRTPEVTCVVVDVSHEDPEVKFNWYVDGVEV

HNAKTKPREEQYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

The underlined portion stands for the signal peptide (with an intron removed) and the portion in bold (underdotted) comprises the CDR.

---

LIGHT CHAIN (LAMBDA)

---

SEQ ID NO: 5

<u>METPAQLLFLLLLWLPESTGQ</u>LVLTQSPSASGTPGQRVTISCSGSSSNIGSSYVYWYQQL

PGAAPRLLIYRNSQRPPGVPDRFSSSKSGTSASLAISGLRSEDEADYYCATWDGSLSGWV

FGGGTKLTVLGQPKAAPSVTLFPPSSEELQANKATLVCLISDFYPGAVTVAWKADSSPVK

AGVETTTPSLQSNNKYAASSYLSLTPEQWKSHRSYSCQVTHEGSTVEKTVAPTECS

---

The underlined portion represents the signal peptide. An intron has been removed for the translation in the signal peptide of the heavy chain. The portion in bold is the constant CH1-hinge-CH2-CH3 region of the antibody.

Moreover, a human chimeric version of a monoclonal rat antibody binding to a soluble form of BSP in plasma was produced.

---

CHIMERIC VERSION OF A RAT MAB (HEAVY CHAIN) - IDK 1

---

SEQ ID NO: 6

<u>MGWSCIILFLVATATGAHS</u>QVQLQESGAELVRPGSSVKISCKAS*GYTFTDF*YMHWVKQGPEQ

GLVWIGRINPANGNTIYAEKFKTKATLTADKSSNTAYMQLSSLTSEDTATYF*CSSA*YWGQ

GTLVTVSSASTKGPSVFPLSPSSKSTSGGTAALGCLVKDYFPEPVTVSWNSGALTSGVHT

FPAVLQSSGLYSLSSVVTVPSSSLGTQTVICNVNHKPSNTKVDKKVEPKSCDKTHTCPPC

PAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHTYQKSLSLSPGK

---

LIGHT CHAIN (KAPPA)

---

SEQ ID NO: 7

<u>METPAQLLFLLLLWLPESTGD</u>ILLTQTPPTSSATIGQSVSISCRSSQSLLDNDGNTYLYW

YLQRPTQSPQLLIYLVSKLRSGVPNRFSGSGSGTDFTLKISGVEAEDLGVYYCVQGTHDP

WTFGGGTKLELKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLRSPVTKSFNRGEC

---

The underlined portion represents the signal peptide. The portion in bold represents the constant CH1-hinge-CH2-CH3 region of the antibody.

| HUMANIZED MAB OF IDK 1 (AF 177.3) - HEAVY CHAIN |
|---|

SEQ ID NO: 8
MGWSCIILFLVATATGAHSQVQLQQSGAEVVKPGASVKVSCKASGYTFTDFYMHWVKQAPEQ

GLEWMGIINPANGNTIYAEKFQGRVTMTADKSTNTVYMELSSLTSEDTATYYCSSAYWGQ

GTLVTVSSASTKGPSVFPLSPSSKSTSGGTAALGCLVKDYFPEPVTVSWNSGALTSGVHT

FPAVLQSSGLYSLSSVVTVPSSSLGTQTVICNVNHKPSNTKVDKKVEPKSCDKTHTCPPC

PAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHTYQKSLSLSPGK

| LIGHT CHAIN (KAPPA) |
|---|

SEQ ID NO: 9
METPAQLLFLLLLWLPESTGDIVMTQTPPSSSVTIGQPASISCKSSQSLLDNDGNTYLYW

YLQKPGQSPQLLIYLVSKRRSGVPDRFSGSGSGTDFTLKISGVEAEDVGVYYCVQGTHDP

WTFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLRSPVTKSFNRGEC

The peptides used for screening the monoclonal rat antibodies for binding to human BSP in plasma were modified with beta-alanine for increasing affinity or peptides with multiple copies of a BSP epitope were used. In this way, we also found a human monoclonal antibody in our proprietary human antibody phagemid library which was then made fully human using recombinant technology (Stefan Dübel, edt., Handbook of Therapeutic Antibodies, Wiley-VCH 2010; ISBN 978-5-527-32902-1). Titration and competition experiments show that the monoclonal antibodies (anti-BSPJDK1 as well as chimeric version thereof, anti-BSP_IDK2 human mAb (clone AF165R4.2-E2) and the humanized antibody anti-BSP_IDK3 (clone AF177.3) bind close by if not the same epitope on human BSP in plasma while the rat mAb (anti-BSP IDK1) has highest affinity.

Example 4—BSP Plasmapheresis Material

There is any clinical evidence that an elimination of circulating BSP via plasmapheresis may cause osteoporosis or a bone disease. In this connection we note that postmenopausal woman suffering from osteoporosis even show elevated levels of serum BSP compared to perimenopausal healthy controls. Moreover, treatment with alendronic Acid® (INN) as well as hormone replacement therapy, which are established therapeutic treatment of osteoporosis, all lead to a reduction of serum BSP levels in postmenopausal women. Thus, there are good reasons to assume that an elimination of BSP from serum or plasma by plasmapheresis can become an accepted therapy for patients suffering from CKD or ESRD.

Moreover, we can relying on proven apheresis materials as there are established processes for the elimination of LDL-cholesterol, lipoprotein and/or apolipoprotein from human plasma. Suitable stationary immunosorbent materials are commercially available, e.g. GLOBAFFIN® and Immunosorba® (Fresenius Medical Care AG, DE). In brief, the therapeutic method for removal of the circulating BSP would require that the blood of the patient is first separated into blood cells and blood plasma using a machine. In a further step the plasma containing the BSP is passed extracorporally through one of more immunosorbent columns. The columns contain the monoclonal antibody against circulating BSP. Whilst the first column is loaded with BSP the second is rinsed (regenerated), to become available again for a further loading cycle. After removal of the circulating BSP, the plasma is mixed again with the blood cells and returned to the patient. Such an extracorporeal treatment of the blood usually takes between three and five hours and can be done using for example the Octo-Nova® machine (Diamed Medizintechnik GmbH, Köln, DE).

We contemplate testing this extracorporeal treatment in animal studies by obtaining a reduction of vascular calcification in adenine-induced nephropathy and a reduction of vascular calcification in diabetic nephropathy, using rats and Zucker diabetic fatty rat. Moreover, a novel companion test is being developed using the antibodies of example 3 to screen for BSP and anti-BSP-antibodies in animal and human blood. As mentioned, the immunosorbent material for a plasmapheresis will be used in the Octo-Nova apheresis system (Diamed Medizintechnik GmbH, Germany). In a later step, we intend to demonstrate that plasma BSP levels are related to mortality in patients with CKD or ESRD. The efficacy and biocompatibility (safety) of the BSP adsorbent material will be proven in an ex vivo study, and finally a tolerability apheresis study phase will be conducted to prove human safety, and reduction of BSP following apheresis in CKD patients. The test antibody (anti-BSP IDK2) was coupled to the stationary phase (Sephadex®) using the NHS method which proved more effective than coupling by BrCN. The coupling was done using a solution of the antibody at 1 mg/ml at 4 degrees Celsius with an NHS-activated column material in borate buffer (BBS, pH 10.0). The coupling efficiency of 78% was determined via the amount of antibody not coupled to the solid phase using the Bradford method. When an antibody concentration of 2 mg/ml was used, the coupling efficiency was 43% which corresponds to 0.86 mg mAb/ml Sephadex®. Thus, an increase of the antibody concentration did not lead to a substantially increased amount of mAb on the stationary phase. When using NHS-activated agarose as stationary phase we obtained a coupling efficiency of 77% in a solution comprising 1 mg/ml mAb and of 62% in a mAb solution comprising 2 mg/ml mAb. Thus, more mAb could be coupled onto agarose than on Sephadex® which can be explained that mAb was also coupled in the interior of the stationary phase.

Figure 10:
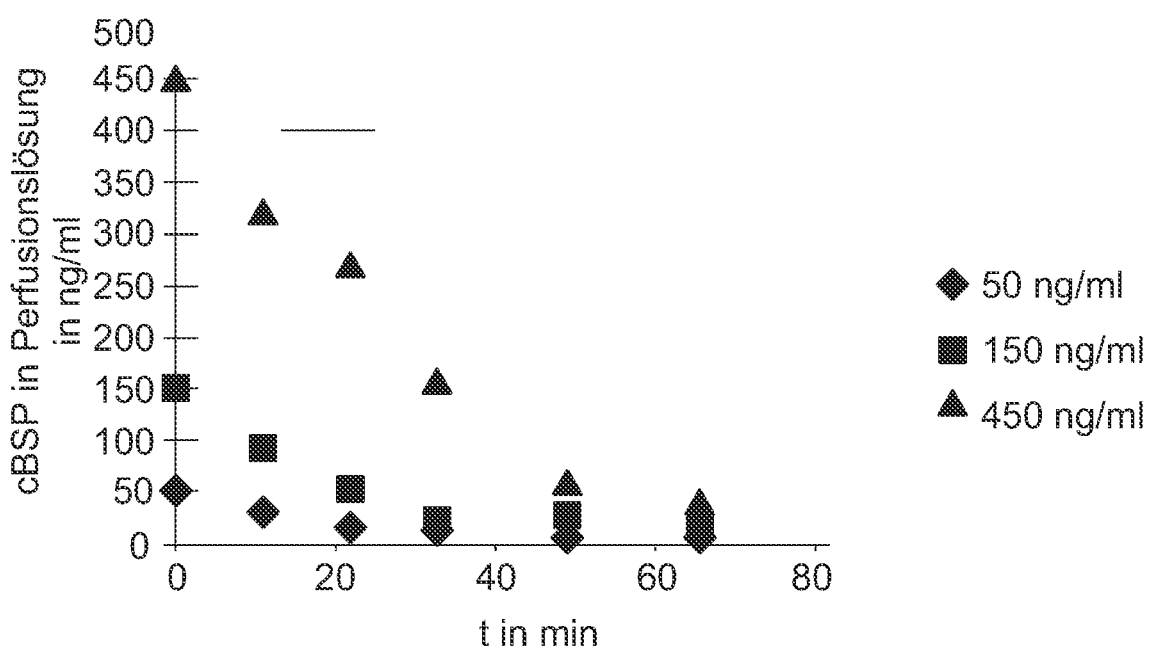
FIG. 10 is a diagram on the binding kinetics of BSP to an anti-BSP mAb agarose.
Figure 11:
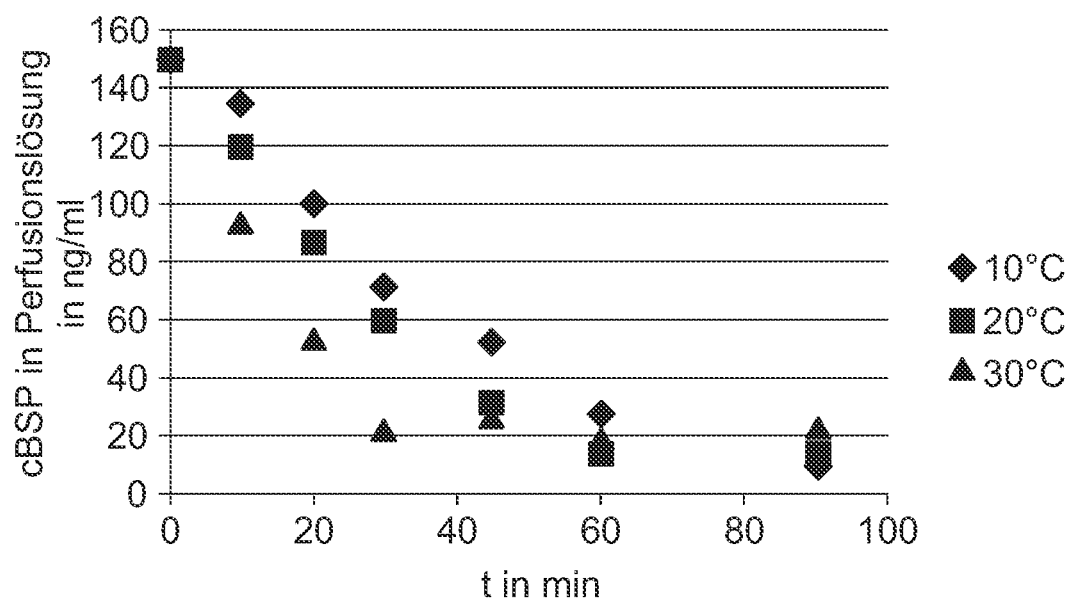
FIG. 11 is a diagram on the effect of temperature on the binding kinetics of BSP to an anti-BSP IDK mAb agarose.

Further parameters of the packed column were fluid flow through in relation to fluid pressure as well as the adsorption kinetics of BSP in relation to temperature and concentration (see FIGS. 10 and 11). For a maximum of BSP binding a temperature of 10 degrees was optimal while the binding kinetics were much better at 30 degrees, allowing shorter application times.

Figure 12:
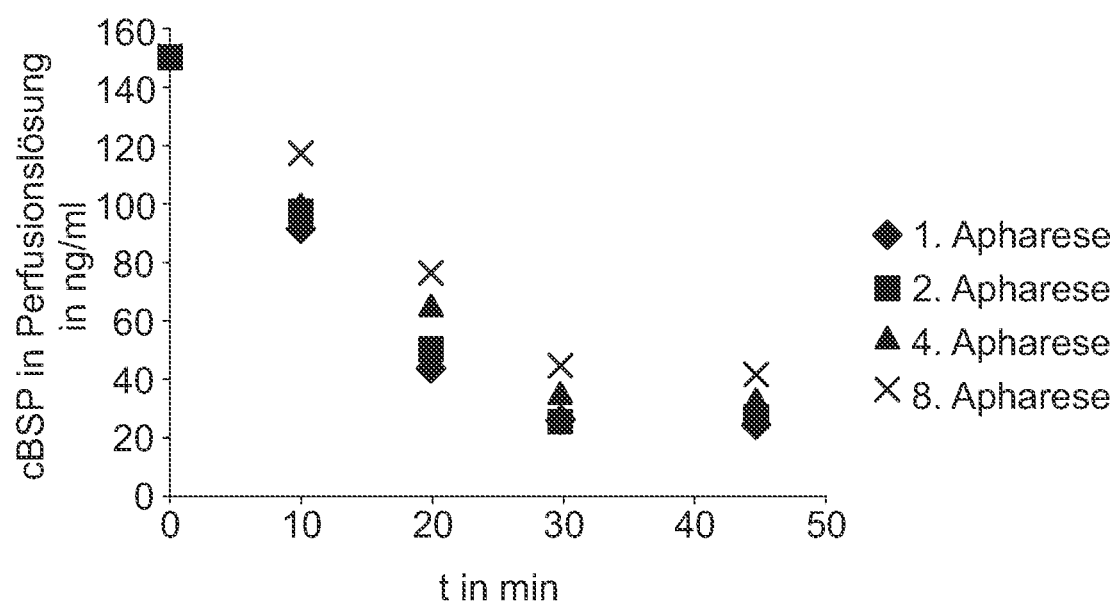
FIG. 12 is a diagram on the numbers of apheresis on the binding kinetics of BSP to an anti-BSP IDK mAb agarose.

The BSP material could be desorbed again from our test columns using a mixture of citrate and vitamin C at a pH of 2.8 to 4. The binding capacity and kinetics only decreased from 85% to 73% in the course of eight rounds of apheresis which is acceptable for these initial tests. The binding kinetics proved equally acceptable (see FIG. 12)

In summary, the optimal parameters for an immunosorbent column material is beaded cross-linked NHS-activated agarose as this gives a reusable and safe column material. The coupling is preferably done in an alkaline carbonate or borate buffer at 4 to 8 degrees Celsius. The binding temperature was optimal at 30 degrees Celsius and about 75 ml blood could be purified from BSP using 15 ml column material.

The invention claimed is:

1. A method of reducing arterial and vascular calcification or treating extracellular tissue and vascular calcification, atherosclerosis, arteriosclerosis, and arterial calcification, comprising the administration of a therapeutically effective amount of a human monoclonal antibody or a humanized monoclonal antibody recognizing an antigen determinant or epitope of human bone-sialoprotein (BSP) which is accessible in blood, plasma or serum and bound by said monoclonal antibody, whose sequence includes the complementary determining regions (CDRs) from:
 the antibody having the amino acid sequences set forth in SEQ ID NO: 4 and 5, or
 the antibody having the amino acid sequences set forth in SEQ ID NO: 6 and 7, or
 the antibody having the amino acid sequences set forth in SEQ ID NO: 8 and 9.

2. The method of claim 1 for treatment of aortic calcifications, atherosclerotic intima lesions and arteriosclerotic intima/media lesions.

3. The method of claim 1 for reduced interstitial renal fibrosis and glomerulosclerosis and reduced media-to-lumen ratio of intrarenal vessels.

4. The method of claim 1 for obtaining reduced cardiac interstitial fibrosis and cardiac perivascular fibrosis.

5. The method of claim 1 for preventing vascular and arterial calcifications in patients with chronic kidney disease (CKD) and end stage renal disease (ESRD).

6. The method of claim 1 for obtaining antifibrotic effects in patients in risk of developing diabetic kidney disease.

* * * * *

SEQUENCE LISTING

```
<160> NUMBER OF SEQ ID NOS: 09

<210> SEQ ID NO 1
<211> LENGTH: 16
<212> TYPE: PRT
<213> ORGANISM: Artificial Sequence
<220> FEATURE:
<223> OTHER INFORMATION: Artificial epitope synthesized for raising
      antibodies against human bone sialoprotein II

<400> SEQUENCE: 1

Tyr Thr Gly Leu Ala Ala Ile Gln Leu Pro Lys Lys Ala Gly Asp Glx
1               5                   10                  15

<210> SEQ ID NO 2
<211> LENGTH: 39
<212> TYPE: PRT
<213> ORGANISM: Artificial Sequence
<220> FEATURE:
<223> OTHER INFORMATION: Epitope synthesized for expression in Listeria
      for raising antibodies against human bone sialoprotein

<400> SEQUENCE: 2

Ser Glu Asn Gly Glu Pro Arg Gly Asp Asn Tyr Arg Ala Tyr Glu Asp
1               5                   10                  15

Glu Tyr Ser Tyr Phe Lys Gly Gln Gly Tyr Asp Gly Tyr Asp Gly Gln
            20                  25                  30

Asn Tyr Tyr His His Gln Glx
        35

<210> SEQ ID NO 3
<211> LENGTH: 55
<212> TYPE: PRT
<213> ORGANISM: Artificial Sequence
<220> FEATURE:
<223> OTHER INFORMATION: Artificial sequence expressed in Listeria to
      trigger antibodies against human bone sialoprotein II

<400> SEQUENCE: 3

Glx Glu Asp Ala Thr Pro Gly Thr Gly Tyr Thr Gly Leu Ala Ala Ile
```

```
1               5                   10                  15
Gln Leu Pro Lys Lys Ala Gly Glx Ser Gly Gly Gly Ser Ala Glx
                20                  25                  30

Gly Ala Lys Lys Pro Leu Gln Ile Ala Ala Leu Gly Thr Tyr Gly Thr
                35                  40                  45

Gly Pro Thr Ala Asp Glu Glx
                50                  55

<210> SEQ ID NO 4
<211> LENGTH: 465
<212> TYPE: PRT
<213> ORGANISM: Rattus rattus

<400> SEQUENCE: 4

Met Gly Trp Ser Cys Ile Ile Leu Phe Leu Val Ala Thr Ala Thr Gly
1               5                   10                  15

Ala His Ser Gln Leu Val Gln Ser Gly Ala Glu Val Lys Lys Pro Gly
                20                  25                  30

Ala Ser Val Lys Val Ser Cys Lys Ala Ser Gly Tyr Thr Phe Thr Gly
                35                  40                  45

Tyr Tyr Met His Trp Val Arg Gln Ala Pro Gly Gln Gly Leu Glu Trp
                50                  55                  60

Met Gly Arg Ile Asn Pro Asn Ser Gly Gly Thr Asn Tyr Ala Gln Lys
65                  70                  75                  80

Phe Gln Gly Arg Val Thr Met Thr Arg Asp Thr Ser Ile Ser Thr Ala
                85                  90                  95

Tyr Met Glu Leu Ser Arg Leu Arg Ser Asp Asp Thr Ala Val Tyr Tyr
                100                 105                 110

Cys Ala Arg Ser Gln Gly Ala Thr Gly Phe Asp Pro Trp Gly Gln Gly
                115                 120                 125

Thr Leu Val Thr Val Ser Ser Ala Ser Thr Lys Gly Pro Ser Val Phe
                130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
                195                 200                 205

Ser Ser Leu Gly Thr Gln Thr Tyr Ile Cys Asn Val Asn His Lys Pro
                210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
                275                 280                 285

Pro Glu Val Lys Phe Asn Trp Tyr Val Asp Gly Val Glu Val His Asn
                290                 295                 300

Ala Lys Thr Lys Pro Arg Glu Glu Gln Tyr Asn Ser Thr Tyr Arg Val
305                 310                 315                 320
```

Val Ser Val Leu Thr Val Leu His Gln Asp Trp Leu Asn Gly Lys Glu
            325                 330                 335

Tyr Lys Cys Lys Val Ser Asn Lys Ala Leu Pro Ala Pro Ile Glu Lys
        340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 5
<211> LENGTH: 236
<212> TYPE: PRT
<213> ORGANISM: Rattus rattus

<400> SEQUENCE: 5

Met Glu Thr Pro Ala Gln Leu Leu Phe Leu Leu Leu Leu Trp Leu Pro
1               5                   10                  15

Glu Ser Thr Gly Gln Leu Val Leu Thr Gln Ser Pro Ser Ala Ser Gly
            20                  25                  30

Thr Pro Gly Gln Arg Val Thr Ile Ser Cys Ser Gly Ser Ser Ser Asn
        35                  40                  45

Ile Gly Ser Ser Tyr Val Tyr Trp Tyr Gln Gln Leu Pro Gly Ala Ala
    50                  55                  60

Pro Lys Leu Leu Ile Tyr Arg Asn Ser Gln Arg Pro Pro Gly Val Pro
65                  70                  75                  80

Asp Arg Phe Ser Ser Ser Lys Ser Gly Thr Ser Ala Ser Leu Ala Ile
                85                  90                  95

Ser Gly Leu Arg Ser Glu Asp Glu Ala Asp Tyr Tyr Cys Ala Thr Trp
            100                 105                 110

Asp Gly Ser Leu Ser Gly Trp Val Phe Gly Gly Gly Thr Lys Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 6
<211> LENGTH: 460
<212> TYPE: PRT
<213> ORGANISM: Artificial sequence
<220> FEATURE:
<223> OTHER INFORMATION: Human chimeric version of a monoclonal rat
      antibody binding to a soluble form of BSP in plasma

<400> SEQUENCE: 6

Met Gly Trp Ser Cys Ile Ile Leu Phe Leu Val Ala Thr Ala Thr Gly
1               5                   10                  15

Ala His Ser Gln Val Gln Leu Gln Glu Ser Gly Ala Glu Leu Val Arg
            20                  25                  30

Pro Gly Ser Ser Val Lys Ile Ser Cys Lys Ala Ser Gly Tyr Thr Phe
        35                  40                  45

Thr Asp Phe Tyr Met His Trp Val Lys Gln Gly Pro Glu Gln Gly Leu
    50                  55                  60

Val Trp Ile Gly Arg Ile Asn Pro Ala Asn Gly Asn Thr Ile Tyr Ala
65                  70                  75                  80

Glu Lys Phe Lys Thr Lys Ala Thr Leu Thr Ala Asp Lys Ser Ser Asn
                85                  90                  95

Thr Ala Tyr Met Gln Leu Ser Ser Leu Thr Ser Glu Asp Thr Ala Thr
            100                 105                 110

Tyr Phe Cys Ser Ser Ala Tyr Trp Gly Gln Gly Thr Leu Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala

```
            340                 345                 350
Lys Gly Gln Pro Arg Glu Pro Gln Val Tyr Thr Leu Pro Pro Ser Arg
            355                 360                 365
Asp Glu Leu Thr Lys Asn Gln Val Ser Leu Thr Cys Leu Val Lys Gly
            370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
            435                 440                 445
Tyr Thr Gln Lys Ser Leu Ser Leu Ser Pro Gly Lys
            450                 455                 460

<210> SEQ ID NO 7
<211> LENGTH: 240
<212> TYPE: PRT
<213> ORGANISM: Artificial Sequence
<220> FEATURE:
<223> OTHER INFORMATION: Humanized chimeric version of a rat monoclonal
      antibody

<400> SEQUENCE: 7

Met Glu Thr Pro Ala Gln Leu Leu Phe Leu Leu Leu Leu Trp Leu Pro
1               5                   10                  15
Glu Ser Thr Gly Asp Ile Leu Leu Thr Gln Thr Pro Thr Ser Ser
            20                  25                  30
Ala Thr Ile Gly Gln Ser Val Ser Ile Ser Cys Arg Ser Ser Gln Ser
            35                  40                  45
Leu Leu Asp Asn Asp Gly Asn Thr Tyr Thr Leu Tyr Trp Tyr Leu Gln
            50                  55                  60
Arg Pro Thr Gln Ser Pro Gln Leu Leu Ile Tyr Leu Val Ser Lys Leu
65              70                  75                  80
Arg Ser Gly Val Pro Asn Arg Phe Ser Gly Ser Gly Ser Gly Thr Asp
            85                  90                  95
Phe Thr Leu Lys Ile Ser Gly Val Glu Ala Glu Asp Leu Gly Val Tyr
            100                 105                 110
Tyr Cys Val Gln Gly Thr His Asp Pro Trp Thr Phe Gly Gly Gly Thr
            115                 120                 125
Lys Leu Glu Leu Lys Arg Thr Val Ala Ala Pro Ser Val Phe Ile Phe
            130                 135                 140
Pro Pro Ser Asp Glu Gln Leu Lys Ser Gly Thr Ala Ser Val Val Cys
145                 150                 155                 160
Leu Leu His Asn Phe Tyr Pro Arg Glu Ala Lys Val Gln Trp Glu Val
                165                 170                 175
Asp Met Ala Leu Gln Ser Gly Asn Ser Gln Glu Ser Val Thr Glu Gln
            180                 185                 190
Asp Ser Lys Asp Ser Thr Tyr Ser Leu Ser Ser Thr Leu Thr Leu Ser
            195                 200                 205
Lys Ala Asp Tyr Glu Lys His Lys Val Tyr Ala Cys Glu Val Thr His
            210                 215                 220
Gln Gly Leu Arg Ser Pro Val Thr Lys Ser Phe Asn Arg Gly Glu Cys
225                 230                 235                 240
```

```
<210> SEQ ID NO 8
<211> LENGTH: 460
<212> TYPE: PRT
<213> ORGANISM: Artificial sequence
<220> FEATURE:
<223> OTHER INFORMATION: humanized mAB of IDK 1 (Heavy Chain)

<400> SEQUENCE: 8

Met Gly Trp Ser Cys Ile Ile Leu Phe Leu Val Ala Thr Ala Thr Gly
1               5                   10                  15

Ala His Ser Gln Val Gln Leu Gln Gln Ser Gly Ala Glu Val Val Lys
            20                  25                  30

Pro Gly Ala Ser Val Lys Val Ser Cys Lys Ala Ser Gly Tyr Thr Phe
        35                  40                  45

Thr Asp Phe Tyr Met His Trp Val Lys Gln Ala Pro Glu Gln Gly Leu
    50                  55                  60

Glu Trp Met Gly Ile Ile Asn Pro Ala Asn Gly Asn Thr Ile Tyr Ala
65                  70                  75                  80

Glu Lys Phe Gln Gly Arg Val Thr Met Thr Ala Asp Lys Ser Thr Asn
                85                  90                  95

Thr Val Tyr Met Glu Leu Ser Ser Leu Thr Ser Glu Asp Thr Ala Thr
            100                 105                 110

Tyr Tyr Cys Ser Ser Ala Tyr Trp Gly Gln Gly Thr Leu Val Thr Val
        115                 120                 125

Ser Ser Ala Ser Thr Lys Gly Pro Ser Val Phe Pro Leu Ala Pro Ser
130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Lys Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365
```

```
Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn Glu
            435                 440                 445

Tyr Thr Gln Lys Ser Leu Ser Leu Ser Pro Gly Lys
    450                 455                 460

<210> SEQ ID NO 9
<211> LENGTH: 239
<212> TYPE: PRT
<213> ORGANISM: Artificial Sequence
<220> FEATURE:
<223> OTHER INFORMATION: humanized mAB of IDK 1 (Light Chain) - kappa

<400> SEQUENCE: 9

Met Glu Thr Pro Ala Gln Leu Leu Phe Leu Leu Leu Leu Trp Leu Pro
1               5                   10                  15

Glu Ser Thr Gly Asp Ile Val Met Thr Gln Thr Pro Ser Ser Ser
                20                  25                  30

Val Thr Ile Gly Gln Pro Ala Ser Ile Ser Cys Lys Ser Ser Gln Ser
            35                  40                  45

Leu Leu Asp Asn Asp Gly Asn Thr Tyr Leu Tyr Trp Tyr Leu Gln Lys
    50                  55                  60

Pro Gly Gln Ser Pro Gln Leu Leu Ile Tyr Leu Val Ser Lys Arg Arg
65                  70                  75                  80

Ser Gly Val Pro Asp Arg Phe Ser Gly Ser Gly Ser Gly Thr Asp Phe
                85                  90                  95

Thr Leu Lys Ile Ser Gly Val Glu Ala Glu Asp Val Gly Val Tyr Tyr
            100                 105                 110

Cys Val Gln Gly Thr His Asp Pro Trp Thr Phe Gly Gly Gly Thr Lys
            115                 120                 125

Val Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
    195                 200                 205

Ala Asp Tyr Glu Lys His Lys Val Tyr Ala Cys Glu Val Thr His Gln
            210                 215                 220

Gly Leu Arg Ser Pro Val Thr Lys Ser Phe Asn Arg Gly Glu Cys
225                 230                 235
```